United States Patent
Bauman et al.

(10) Patent No.: US 8,935,280 B2
(45) Date of Patent: Jan. 13, 2015

(54) MEDICAL IMAGE IMPORTER AND METHOD

(75) Inventors: Aaron A. Bauman, Smithville, OH (US); Garvin Seto, Highland Hts, OH (US); Gary Enos, Hudson, OH (US); Gary Keefe, Brecksville, OH (US); Michael Lustig, Parma, OH (US); Ross Goodman, Solon, OH (US)

(73) Assignee: Codonics, Inc., Middleburg Heights, OH (US)

( * ) Notice: Subject to any disclaimer, the term of this patent is extended or adjusted under 35 U.S.C. 154(b) by 203 days.

(21) Appl. No.: 12/614,329

(22) Filed: Nov. 6, 2009

(65) Prior Publication Data

US 2010/0114951 A1 May 6, 2010

Related U.S. Application Data

(60) Provisional application No. 61/111,942, filed on Nov. 6, 2008.

(51) Int. Cl.
*G06F 19/00* (2011.01)

(52) U.S. Cl.
CPC ................................. *G06F 19/321* (2013.01)
USPC .......................................................... 707/770

(58) Field of Classification Search
USPC .......................................................... 707/770
See application file for complete search history.

(56) References Cited

U.S. PATENT DOCUMENTS

| | | | |
|---|---|---|---|
| 5,899,998 A | 5/1999 | McGauley et al. | |
| 6,438,533 B1 * | 8/2002 | Spackman et al. | 706/45 |
| 6,523,009 B1 | 2/2003 | Wilkins | |
| 6,988,075 B1 | 1/2006 | Hacker | |
| 7,039,628 B2 | 5/2006 | Logan, Jr. | |
| 7,275,220 B2 | 9/2007 | Brummel et al. | |
| 7,295,988 B1 | 11/2007 | Reeves | |
| 7,395,215 B2 | 7/2008 | Grushka | |
| 7,438,233 B2 | 10/2008 | Leiper | |
| 7,523,505 B2 * | 4/2009 | Menschik et al. | 726/26 |
| 2002/0016718 A1 * | 2/2002 | Rothschild et al. | 705/2 |
| 2002/0029157 A1 | 3/2002 | Marchosky | |
| 2002/0120470 A1 | 8/2002 | Trice, Sr. | |
| 2002/0156650 A1 | 10/2002 | Klein et al. | |
| 2003/0040940 A1 | 2/2003 | Nehammer | |
| 2003/0208382 A1 | 11/2003 | Westfall | |
| 2005/0075909 A1 | 4/2005 | Flagstad | |
| 2005/0216313 A1 | 9/2005 | Claud et al. | |
| 2005/0288568 A1 * | 12/2005 | Pan | 600/407 |
| 2006/0115135 A1 * | 6/2006 | Dehmeshki et al. | 382/128 |
| 2007/0050216 A1 | 3/2007 | Wright et al. | |
| 2008/0059236 A1 | 3/2008 | Cartier | |
| 2008/0250506 A1 | 10/2008 | Rabischong et al. | |
| 2009/0012817 A1 | 1/2009 | Squires et al. | |
| 2009/0055924 A1 | 2/2009 | Trotter | |

* cited by examiner

Primary Examiner — Amresh Singh
(74) Attorney, Agent, or Firm — Pearne & Gordon LLP

(57) ABSTRACT

Provided are a medical information importer and method for importing medical information into a network-accessible database. The medical information importer includes a housing includes with an external stand-alone form factor, the housing including an interface for receiving a portable computer-readable medium storing medical information. An information reading component is provided for reading the medical information from the portable computer-readable medium when operatively connected to the interface. A computer-readable memory in communication with the information reading component stores, at least temporarily, the medical information read by the reading component under the direction of a controller. And a network interface connects the medical information importer to a communication network without a local connection between the medical information importer and a computer terminal including a display device for viewing the medical information.

11 Claims, 7 Drawing Sheets

MEDICAL IMAGE IMPORTER AND METHOD

This application claims the benefit of U.S. Provisional Application No. 61/111,942, filed Nov. 6, 2008, which is incorporated in its entirety herein by reference.

BACKGROUND OF THE INVENTION

1. Field of the Invention

This application relates generally to a method and apparatus for importing medical information into a computer-accessible database, and more specifically to a method and apparatus for importing DICOM standard compliant medical images and related information from a portable computer-readable medium into a PACS or other computer-accessible memory over a communication network.

2. Description of Related Art

Traditional medical studies often include comprehensive documentation of the subject that is the focal point of the study. Many such studies include at least one of a medical image such as an x-ray, PET scan, CT scan or the like; textual information in a report related to the focal point of the study; and information about the patient and his or her care during the study. For example, the focal point of the study may be the lower back of a patient. During an examination a treating physician may send the patient to have a MRI conducted on the portion of the patient's lower back that is the focal point of the study. The MRI, a written report, and other information collected by the treating physician or others who conducted the MRI could all be included as part of the study being conducted on the patient's lower back. Medical images such as the MRI, information related to the focal point of the study such as the treating physician's report, and any other information about the patient and his or her care is collectively referred to herein as "Medical Information".

When Medical Information about a patient is required to be transferred from one entity to another, the patient is often provided with a hardcopy of the Medical Information to be given to the desired recipient. Hardcopies of medical images have traditionally been printed onto film sheets and reports printed onto paper, for example, to be manually delivered in a tangible form to the recipient. Although the hardcopies can convey the necessary information that must be reviewed by the specialist to evaluate the patient's condition, the information in the report must be manually entered into the specialist's computer database. Further, the film sheets can be scanned or otherwise captured in an electronic image for archival purposes.

More recently, the medical industry has moved to storing Medical Information in an electronic format onto a portable computer-readable medium such as a CD, DVD, USB flash drive, etc. . . . from where they can be retrieved and viewed using a computer workstation loaded with compatible image viewer software. In this way, the Medical Information can be retrieved and viewed using a computer without printing a hardcopy, but the computer-readable medium storing the Medical Information must still be delivered to the intended recipient to have the Medical Information stored in the recipient's medical record database.

As an example of the process for transferring Medical Information from a first medical care provider to a second medical care provider, the patient can be given a CD storing the patient's MRI or other Medical Information by the first provider. The patient, upon arriving at the second provider's facility, can hand the CD to a receptionist who is to manually select and copy the Medical Information from the CD into the second provider's database. To accomplish this, the receptionist will typically insert the CD into a computer terminal located at the reception area. Using that same computer terminal, the receptionist will browse the contents of the CD on a monitor locally connected to that computer terminal at the reception area and select those files that are to be saved within the second provider's database, which is usually a network-accessible computer-readable medium. The receptionist must also properly identify the file location within the second provider's database where medical information for this particular patient is to be stored so the Medical Information can be associated with the patient. The receptionist must also manually save the Medical Information being imported from the CD using the computer terminal at the reception area in a way that does not overwrite existing medical information stored within the second provider's database. After performing the steps outlined above the receptionist then stores the Medical Information directly from the CD to its ultimate storage destination in the second provider's database of medical records from where it can be retrieved for clinical purposes.

BRIEF SUMMARY

Accordingly, there is a need in the art for a method and apparatus for at least partially automating the import of Medical Information recorded on portable computer-readable medium into a medical care provider's network. The medical care provider's network can optionally be a medical care facility's picture archiving and communication system ("PACS"), including a PACS server storing a PACS image database or other DICOM store destination, a workstation, or other computer-readable storage device for storing the Medical Information.

According to one aspect, the subject application involves a medical image importer including a housing comprising an external stand-alone form factor for being operatively connected to a communication network via a network interface without a local connection to a computer terminal including a display device. An optical drive can be provided to the housing for reading from an optical computer-readable medium introduced to the optical drive a medical image associated with a patient captured by a medical modality. A local computer-readable memory is provided to the housing in communication with the optical drive for storing, at least temporarily, the medical image read by the optical drive. A controller is provided and is operable to execute computer-executable logic for controlling operation of the medical image importer. An instructional computer-readable memory stores computer-executable instructions to be executed by the controller for performing a method that includes querying a remotely-located patient information database in communication with the communication network storing patient information associated with the medical image to be transmitted from the medical image importer. Querying includes transmitting the patient information associated with the medical image over the communication network to identify a patient entry in the patient information database at a time of the query. Content is to be served over the communication network to generate a display on a remotely-located computer terminal. The display is presentable in a web-browser application on the remotely-located computer terminal to display at least a portion of information associated with the patient entry stored in the patient information database returned in response to said querying. In the local computer-readable memory, the patient information read by the optical drive is to be updated based on the information associated with the patient entry in the patient information database returned in response to the querying.

The medical image is associated with the patient information updated based on the information associated with the patient entry in the patient information database, and the patient information updated based on the information associated with the patient entry in the patient information database and the medical image are transmitted over the communication network to be stored in the PACS image database.

According to another aspect, the subject application involves a medical information importer including a housing with an external stand-alone form factor. The housing includes an interface for receiving medical information from at least one of a portable computer-readable medium and a medical modality over a communication network. An information reading component reads the medical information from the portable computer-readable medium when the portable computer-readable medium is operatively connected to the interface. A computer-readable memory in communication with the information reading component stores, at least temporarily, the medical information read by the reading component. A controller controls storage of the medical information on the computer-readable memory, and a network interface connects the medical information importer to a communication network without a local connection between the medical information importer and a computer terminal including a display device for viewing the medical information. The medical information is to be transmitted over the communication network to be associated with patient information stored in a database residing on a remotely-located computer-accessible memory.

According to another aspect, the subject application involves a method of storing medical information about a patient into a database. According to the method, medical information is received using a medical information importer comprising an interface for receiving a portable computer-readable medium and a local computer-readable memory and a network interface for operatively connecting the medical information importer to a communication network. In response to the receiving, the medical information received is stored, at least temporarily, in the local computer-readable memory of the medical information importer. Content is served from the medical information importer over the communication network for generating a display on a remotely-located computer terminal enabling a user to input a request for the medical information stored on the local computer-readable memory to be transmitted over the communication network. The request to transmit the medical information stored in the local computer-readable memory provided to the medical information importer over the communication network to be stored in the database is received over the communication network, and the database resides on a remotely-located computer-accessible memory. In response to receiving the request, the medical information is transmitted over the communication network to be stored in the database and associated with the patient.

According to another aspect, the subject application involves a method of reconciling imported medical information about a patient with existing information about the patient stored in a database. The method according to the present aspect includes receiving the medical information using a medical information importer comprising an interface for receiving a portable computer-readable medium, and a local computer-readable memory and a network interface for operatively connecting the medical information importer to a communication network. In response to receiving the medical information, the received medical information is stored, at least temporarily, in the local computer-readable memory of the medical information importer. The method also includes transmitting over the communication network a request for information associated with an existing patient record stored in the database. Such a request includes a predetermined criterion included in the medical information stored in the local computer-readable memory that is to be used to select the existing patient record in the database. The method also includes updating at least one of: the medical information stored in the local computer-readable memory of the medical importer based on the information associated with the existing patient stored in the database returned in response to the request, and the existing patient stored in the database based on the medical information stored in the local computer-readable memory of the medical information importer.

According to another aspect, the subject application involves a method of importing medical information about a patient into a communication network and storing the medical information in a computer-accessible memory. The method according to the present aspect includes using a medical information importer located at a first location, storing the medical information on a portable computer-readable medium introduced to the medical information importer, at least temporarily, in a local computer-readable memory in communication with the medical information importer before the medical information is transmitted over the communication network. A first party is granted permission by the medical information importer to view the medical information stored in the local computer-readable memory using a first computer terminal, but is restricted from editing the medical information stored in the local computer-readable memory. Similarly, a second party is granted permission to view and edit medical information stored in the local computer-readable memory using a second computer terminal that is remotely located from the first computer terminal and in communication with the medical information importer over the communication network. The second party is granted permission to transmit the medical information over the communication network to be stored in a database residing on a remotely-located computer-accessible memory that is accessible via the communication network.

According to another aspect, the subject application involves a system for importing medical information about a patient and storing the medical information in a computer-accessible memory. The system includes a plurality of sources that are operable to transmit medical information over a communication network. At least one of the sources comprises a medical information importer that is configured to automatically transmit the medical information, without operator intervention, over the communication network in response to receiving the medical information within a local computer-readable memory operatively connected to the medical information importer. A central medical information importer is operatively connected to the communication network to receive the medical information from each of the sources over the communication network. The central medical information importer is assigned a network address to be used by a remotely-located computer terminal for accessing the medical information stored on the computer-readable memory over the communication network. The central medical information includes a computer-readable memory storing computer-executable instructions to be executed for performing a method that includes transmitting a request over the communication network for existing information associated with a patient from a database residing on a remotely-located computer-accessible memory. The method also includes transmitting over the communication network to a remotely-located computer terminal, content for presenting a portion of the medical information adjacent to the existing information.

The medical information is reconciled with the existing medical information in the database, associating with the patient, and stored in the database.

According to another aspect, the subject application involves a method of importing medical information to be stored in a database residing on a remotely-located computer-accessible memory. The method includes using a medical information importer, receiving the medical information and storing the medical information that is received, at least temporarily, in a local computer-readable memory in communication with the medical information importer. In response to receiving the medical information, automatically transmitting the medical information over a communication network without operator intervention to be stored on the computer-accessible memory that is remotely located from the medical information importer.

According to another aspect, the subject application involves a method of importing medical information about a patient that is formatted according to a medical imaging standard into a communication network and storing the medical information in a computer-accessible memory. The method according to this aspect includes using a medical information importer located at a first location to receive the medical information in the medical imaging standard and locally storing the medical information in a computer-readable memory in local communication with the medical information importer. A request to reconcile a portion of the medical information is received over a communication network from a first computer terminal that is remotely located from the medical information importer. In response to receiving the request, a database stored on a computer-accessible memory operatively connected to the communication network is queried for an entry in the database associated with the patient. The portion of the medical information locally stored by the computer-readable memory in local communication with the medical information importer is updated based on a result of said querying. A request to store the medical information in at least one of a different database and the database that was queried is requested over the communication network from a second computer terminal that is remotely located from the medical information importer and the first computer terminal. And the medical information is transmitted over the communication network to be stored.

According to another aspect, the subject application involves a method of reconciling imported medical information about a patient with existing information about the patient stored in a database. The method includes receiving the medical information using a medical information importer comprising an interface for receiving a portable computer-readable medium, a local computer-readable memory and a network interface for operatively connecting the medical information importer to a communication network. In response to receiving the medical information, storing the medical information received in the local computer-readable memory of the medical information importer. A database stored on a computer-accessible memory operatively connected to the communication network is queried for an entry in the database associated with the patient. The query includes transmitting a predetermined criterion included in the medical information for selecting the entry in the database from among a plurality of entries and comparing the predetermined criterion with information associated with the plurality of entries in the database. Based on this comparison, a likelihood that the medical information received is to be associated with each of the plurality of entries in the database is determined. The quantity of query results returned is limited to a portion, but less than all of the plurality of entries in the database, having a greatest likelihood of being associated with the patient that is associated with the medical information.

According to another aspect, the subject application involves a medical information importer including a housing with an external stand-alone form factor, the housing comprising an interface for receiving medical information from at least one of a portable computer-readable medium and a medical modality over a communication network. The importer also includes an information reading component for reading the medical information from the portable computer-readable medium when the portable computer-readable medium is operatively connected to the interface. A computer-readable memory in communication with the information reading component is utilized for storing, at least temporarily, the medical information read by the reading component. A controller controls storage of the medical information on the computer-readable memory, and a network interface connects the medical information importer to a communication network without a local connection between the medical information importer and a computer terminal including a display device for viewing the medical information. The medical information is to be transmitted over the communication network to be associated with patient information stored in a database residing on a remotely-located computer-accessible memory.

According to yet another aspect, the subject application involves a method of importing medical information about a patient and storing the medical information in a computer-accessible memory. The method includes, using a medical information importer, receiving medical information from a plurality of different sources operatively connected to transmit medical information over a communication network, wherein the plurality of different sources comprise at least one of: (i) a medical information importer that is configured to automatically transmit the medical information, without operator intervention, over the communication network in response to receiving the medical information within a local computer-readable memory operatively connected to the medical information importer; (ii) a medical modality in communication with the communication network for transmitting the medical information captured by the medical modality over the communication network; and (iii) a remotely-located computer terminal operatively connected to the communication network. The medical information received from the plurality of different sources is to be stored in a computer-readable memory locally connected to the medical information importer. A request to access the medical information stored on the computer-readable memory is received from a remotely-located computer terminal over the communication network. A patient information database is queried over the communication network for an entry in the database that is associated with the patient. The method also includes transmitting, over the communication network to the remotely-located computer terminal, content for presenting a portion of the medical information adjacent to information associated with the entry in the database returned by the query. The medical information is reconciled with the information associated with the entry in the database and the medical information is associated with the entry for the patient in the database. The medical information is stored in a desired computer-accessible memory operatively connected to the communication network.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1A:
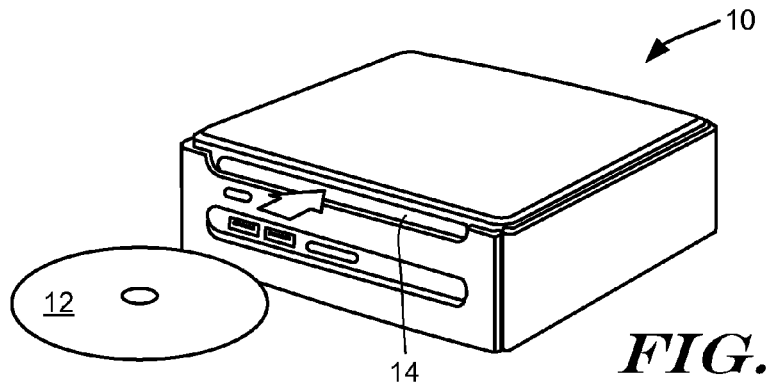
FIG. 1A is an illustrative embodiment of a portable Medical Information importer according to an aspect of the present invention.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

The subject application relates to a Medical Information importer 10, shown in FIG. 1A, that is operable to automate the importation, and optionally the reconciliation and storing of Medical Information stored on a portable computer-readable medium into a computer-accessible database over a communication network. The Medical Information importer 10 has a generally compact and portable form factor that can be hand carried and removably connected as desired to a PACS network 104 (FIG. 3B) as described in detail below. Further, the Medical Information importer 10 can be a self contained, modular network device that is operable to communicate via the communication network without being operatively connected directly to a local, host computer. To facilitate communications over the communication network the Medical Information importer 10 can be assigned a network address such as an IP address. The IP or other network address, static or dynamic, allows remotely-located computer terminals to access the Medical Information and other content stored on the Medical Information importer 10 over a communication network such as a local area network "LAN", a wide-area network "WAN" such as the Internet, or a combination thereof. In this manner the Medical Information importer 10 can act as a server, serving content over the PACS network 104 to be used for generating the displays within a web browser application such as Internet Explorer and the like as described below. The Medical Information importer 10 can be operable independent of a local, host computer and can read, reconcile and store Medical Information into a PACS server 106 or any other DICOM compliant recipient in the PACS network 104 as described in detail below, optionally without a display device or mouse connected locally, or other local computer connection. However, for the sake of brevity the embodiments below describe storing the Medical Information into a database residing on the PACS server 106, which is remotely-located from the Medical Information importer 10.

Figure 1B:
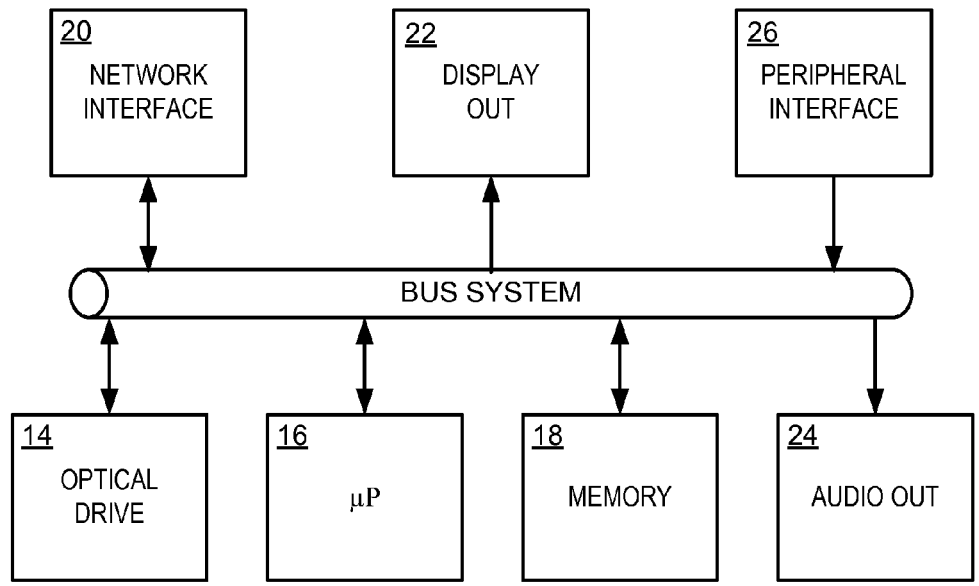
FIG. 1B is a block diagram illustrating internal components of a Medical Information Importer for reading Medical Information from a computer-readable medium and optionally reconciling the Medical Information with existing information in a computer-accessible database.

The term "local" is used herein to refer to connections between the Medical Information importer 10 and a display device, mouse, computer terminal, etc. . . . that are direct connections such as via a USB cable, DVI cable, serial cable, and other such direct connections for communicating independently of the communication network. A local connection allows the Medical Information importer 10 to communicate directly with the device to which it is locally connected, without transmitting information or content over the LAN and/or WAN to accomplish such a local communication. Thus, for embodiments such as that shown in FIG. 2, where there is no local communication to a display device or computer terminal, the Medical Information importer 10 is network connected to other resources over the LAN, the WAN, or both. Such a configuration includes a housing with an external, stand-alone form factor, i.e., can be placed where desired, not just adjacent a networked computer terminal for independent operation and communicating with other network resources over the communication network. The Medical Information importer 10 according to such embodiments simply acts as an input terminal to the PACS network 104 that is remotely-located from the other networked resources. Likewise, a "local" computer-readable memory such as memory device 18 (FIG. 1B) described below is a computer-readable memory locally provided to store Medical Information imported by the Medical Information importer 10. For example, the memory device can be an internal hard disk drive provided to the Medical Information importer 10, or any other suitable memory device for storing electronic data.

As described above, the Medical Information includes one or more studies, which can optionally include files that are compliant with a standard medical file format such as the DICOM standard. The Medical Information importer 10 can optionally act in a DICOM SCP capacity, meaning that the Medical Information importer 10 is a destination similar to a server for receiving incoming Medical Information from a source of the Medical Information. Similarly, the Medical Information importer 10 can optionally act in a DICOM SCU capacity within the PACS network 104, meaning that the Medical Information importer 10 is a client for transmitting the Medical Information received from an outside source over the PACS network 104 to a storage destination such as a PACS server 106, for example. Alternate embodiments include a Medical Information importer 10 that can act in both the DICOM SCP capacity and the DICOM SCU capacity. The PACS server 106 can optionally store a dedicated PACS image database, for example. The one or more studies to be received and/or transmitted by the Medical Information importer 10 can include at least one of:

- a medical image captured by an imaging modality such as an x-ray device, MRI scanner, PET scanner, or CT scanner, for example;
- a medical data plot captured by a plotting modality such as an electrocardiograph, for example;
- a video clip such as video of a surgical procedure being performed and video captured by a medical modality;
- an audio track captured by an acoustic modality such as an ultrasound machine for example; and
- text data related to the patient, medical image, medical data plot, audio track, or any combination thereof.

The Medical Information importer 10 can optionally be dedicated to primarily receive and transmit one or more of the different types of Medical Information. For example, the Medical Information importer 10 can be primarily a medical image importer for receiving and transmitting primarily different types of medical images to be stored in a PACS image database in a manner similar to that described in detail below.

To clearly describe the illustrative embodiments, the computer-readable medium in FIG. 1A is an optical storage medium referred to herein as a disc 12. The disc 12 can be any optical storage medium, including but not limited to, CD-R, CD-RW, DVD-R, DVD-RW, DVD+R, DVD+RW, Blu-ray Disc, HD-DVD, and the like. In addition to, or in lieu of the disc 12 for storing the Medical Information, another suitable portable computer-readable medium such as a USB flash memory, portable hard drive, and the like may be used.

Figure 3A:
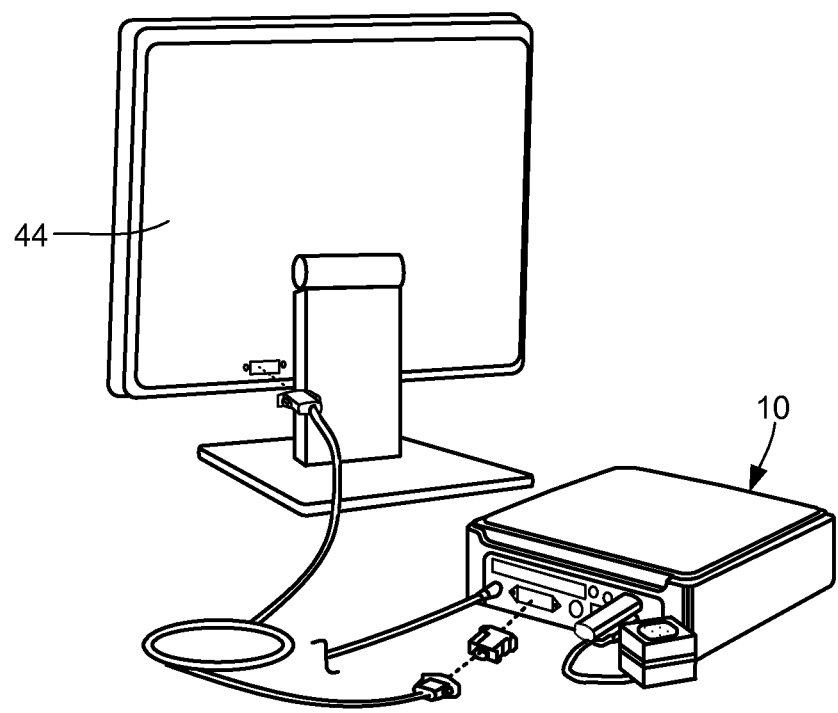
FIG. 3A is an alternate embodiment of a portable Medical Information importer including an optional local connection to a monitor that can be a stand alone display device or operatively coupled to a local workstation.
Figure 3B:
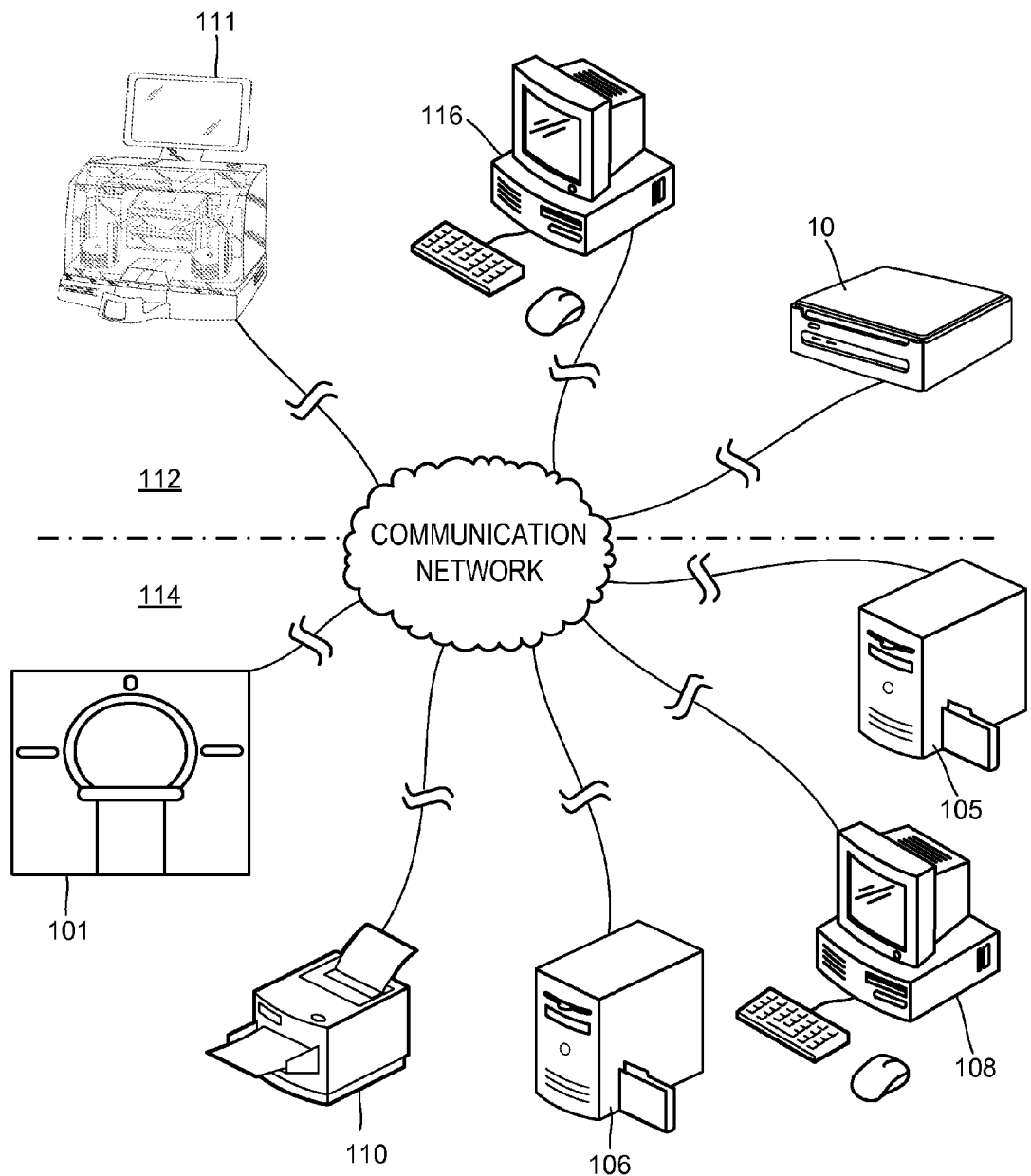
FIG. 3B is an illustrative embodiment of a PACS network comprising a Medical Information importer

For the embodiment shown in FIG. 1A, the Medical Information importer 10 includes an optical drive 14 for receiving the disc 12 and reading the information stored thereon to be imported into the PACS network 104 (FIG. 3B). Shown best in FIG. 1B, a microprocessor 16 is operable to execute computer-readable logic such as embedded firmware, for example, or other suitable computer-executable logic stored in a memory device 18 and control the reading of the Medical Information from the disc 12. The steps and functions described as being performed herein by the Medical Information importer 10 can optionally be executed, controlled, initiated or any combination thereof through the microprocessor's execution of the computer-executable instructions stored in the memory device 18 or other suitable computer-readable memory. The term "component" as used herein can refer to hardware of the Medical Information importer 10, a portion of the computer-executable instructions, or a combination thereof to preform the various steps and functions described and claimed.

The memory device 18 can be a magnetic hard drive, flash-based memory, embedded memory within the microprocessor 16, or any other suitable memory that can at least temporarily store the Medical Information and optionally store the BIOS and other computer-executable logic executed to control functions performed by the Medical Information importer 10. The memory device 18 can optionally be a single computer-readable memory, a memory array comprising a plurality of memory modules, or a memory device 18 partitioned into a plurality of portions and a different portion used for storing the Medical Information and the computer-executable logic. The portion of the memory device 18 storing the computer-executable instructions to be executed by the Medical Information importer 10 is interchangeably referred to herein as an instructional computer-readable memory. Included in the computer executable logic stored in the memory device 18 is an auto-run instruction that automatically, without operator intervention, initiates the reading of the Medical Information from the disc 12 in response to insertion of the disc 12 in the optical drive 14 by the operator. According to alternate embodiments, the memory device 18 can store virus scan logic that can be executed by the microprocessor 16 to scan at least a portion of the Medical Information to be read from the disc 12 and imported into the PACS network 104. According to alternate embodiments, the virus scan can be performed before the Medical Information is read from the disc 12 to determine whether a virus or other malicious code exists before it is read and stored in the memory device 18 of the Medical Information importer 10, after the Medical Information is read from the disc 12 and stored in the memory device 18, or in real time while the Medical Information is being read from the disc 12 and stored in the memory device 18.

A network interface 20, display output port 22, audio output port 24 and administrative interface 26 are also operatively connected to communicate with the other internal components under the control of the microprocessor 16 via a bus system 28. The Medical Information read from the disc 12 is transmitted from the optical drive 14 over the bus system 28 to the network interface 20. From there it is transmitted via a RJ-45 CAT6 or other suitable Ethernet network cable 30 (FIG. 2), or via a wireless network connection (not shown) such as the 802.1x standard promulgated by the Institute of Electrical and Electronics Engineers ("IEEE"), for example, to a compatible jack 32 through which the Medical Information can be introduced into the PACS network 104.

Figure 2:
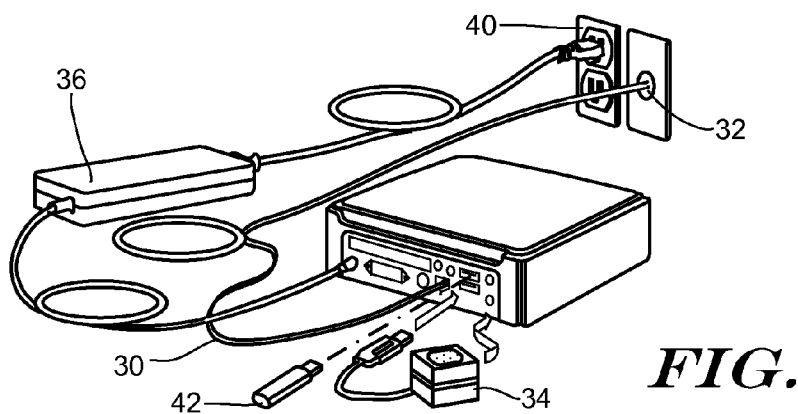
FIG. 2 is an illustrative embodiment of the connectivity of the portable Medical Information importer in FIG. 1.

An external speaker 34 shown in FIG. 2 can be operatively connected to the audio output port 24 to present audible acknowledge sounds to the operator indicating a completion of the importation of the Medical Information to the PACS network 104, indicating an error condition, present instructions to the operator, and the like. An external power supply 36 can also be provided to convert AC mains power from a wall jack 40 to DC power to be delivered to the Medical Information importer 10.

A USB flash memory device referred to herein as a Smart Drive 42 (FIG. 2) can be connected to the administrative interface 26 via a USB 2.0 port, for example. The Smart Drive 42 stores system information such as configuration data for establishing the operating parameters of the Medical Information importer 10 during operation, and can optionally replace or supplement the memory device 18 of the Medical Information importer 10. The Smart Drive 42 can also store license codes or product keys for the computer-executable logic to be executed by the microprocessor 16, thereby acting as a security feature that interferes with operation of the Medical Information importer 10 without the Smart Drive 42 installed. The Smart Drive 42 can store one or more profiles that define parameters for the system configuration; user accounts; site parameters; job profiles that control how imported Medical Information will be processed by the Medical Information importer 10 and introduced into the PACS network 104; Match Rule profiles that define the fields on which a query will be performed when looking for patients associated with the Medical Information being imported and reconciled; a Reconciler Profile that defines which Modality Work List ("MWL") and/or Query/Retrieve servers to include in a reconcile query, and the query rules to be applied during said reconcile query; and a destination profile, which defines a unique set of parameters (e.g., destination's host IP address, TCP port number, called AE title, etc. . . . ) for sending studies to a destination. Since the Smart Drive 42 is removably connectable to the Medical Information importer 10, it can be operatively connected to different Medical Image importers to establish a desired configuration at different Medical Information importers 10. But since the Smart Drive 42 includes key codes and license information required to operate the Medical Information importer 10, only one Medical Information importer 10 can be operated by a particular Smart Drive 42 at any given moment.

The MWL, for example, includes of a set of entries, each containing data for a given patient and study. It represents the tasks for each device in the radiology office to do in a given time period with each entry representing a given task. The worklist resides on a server connected to the PACS network such as the RIS server 105 or PACS server 106, for example, but could alternately reside on a Health Information System ("HIS") server or even a standalone workstation. The MWL can be queried by sending a subset of the Medical Information, such as patient information for example, to the server, and the server responds with matching entries from the MWL.

The smart drive 42 can configure the Medical Information importer 10 to grant permission to a plurality of different parties with respect to accessing the Medical Information. Parties can be designated as "Readers," "Reconcilers," "Importers" and "Administrators" according to one embodiment. For instance, a receptionist or other clerical staff member affiliated with a healthcare provider may be granted permission to access the Medical Information once stored locally by the Medical Information importer 10. Readers can be granted permission to input an optical disc or other portable computer-readable medium into the Medical Information importer 10 to initiate reading of the Medical Information from the Medical Information importer 10 and storage of the Medical Information, at least temporarily in a local computer-readable memory referred to interchangeably herein as the memory device 18. The configuration of the Medical Information importer 10 can also cause execution of computer-executable instructions to grant the Reader permission to retrieve the Medical Information stored in the memory device 18 over a communication network such as the PACS network 104 using a computer terminal. However, parties accessing the Medical Information importer 10 as a Reader can be restricted, and thereby prohibited from editing, updating or otherwise modifying the Medical Information locally stored by the Medical Information importer 10. The computer terminal used by the Reader can optionally be placed at a reception area of the healthcare provider. Another party, referred to herein as a Reconciler, can access the Medical Information importer 10 over the communication network using a different computer terminal and be granted permission in response to execution of the computer-executable instructions to read and review the Medical Information locally stored by the Medical Information importer 10. Thus, during reconciliation of the locally stored Medical Information with information about the patient retrieved from a database as described in detail below, the locally stored Medical Information can be updated within the memory device 18 of the Medical Information importer 10 before being stored in the PACS server 106. Although the Reconciler can edit, update and otherwise modify the Medical Information locally stored by the Medical Information importer 10, the Reconciler is restricted, and thus prohibited by the Medical Information importer 10 from transmitting the Medical Information from the memory device 18 to be stored in the PACS server 106. The Reconciler typically has greater authority at the healthcare provider than the clerical Reader.

Yet another party, such as a physician affiliated with the healthcare provider, can be granted the permissions of an Importer by the Medical Information importer 10. The Importer has the ultimate responsibility to transmit the Medical Information, as updated by the Reconciler, from the Medical Information importer 10 over the communication network to be stored in the PACS server 106. The Importer can also optionally be granted the permissions of the Reader and Reconciler as well.

And a party, referred to herein as an Administrator, can be granted unrestricted access to the Medical Information and the permissions of the Reader, Reconciler and Importer. The Administrator can also optionally be granted permission to edit, change or otherwise modify the configuration of the Medical Information importer 10. For example, the Administrator can assign roles to personnel and configure the Medical Information importer 10 to grant the appropriate permissions and restrict access to the Medical Information locally stored in the memory device 18 according to those roles. Thus, the Medical Information importer 10 can control access to the Medical Information locally resident in the memory device 18 based on the role assigned to each party.

Each party can optionally be granted their respective permissions based on information input into the Medical Information importer 10 over the communication network to gain access to the Medical Information. For example, each party, upon entering a URL, IP address, or other suitable locator into a web-browser application running on a computer terminal to communicate with the Medical Information importer 10, can be prompted to enter a login ID, password, or both. Based on the information input, the Medical Information importer 10 can grant the appropriate permissions corresponding to that information. Similarly, the Medical Information importer 10 is also operable to restrict the ability of parties to perform functions outside of the permissions granted. For example, the Medical Information importer 10, by executing computer-executable logic, can grant permission to the Reconciler to save and update Medical Information locally stored on the local computer-readable memory waiting to be transmitted and imported into the PACS server 106, for example. But the Medical Information importer 10 can execute computer-executable logic to prohibit the Reconciler from transmitting the Medical Information over the PACS network 104 to be imported and stored in the PACS server 106.

The optional display output port 22 can be provided to the Medical Information importer 10 to establish a local connection with a display device 44, as shown in FIG. 3A. The display device 44 allows the operator to view the screens described below locally (i.e., directly from the Medical Information importer 10 and not connected to the Medical Information importer 10 only over the PACS network 104 or other communication network).

The PACS network 104 shown in FIG. 3B can be viewed as including a clerical side 112 and a clinical side 114. The clerical side 112 can include a computer terminal 116 located at a reception area of the healthcare provider, and optionally the Medical Information importer 10 that patients or a receptionist can use to initially introduce the Medical Information into the PACS network 104. The clerical side 112 can be utilized to perform clerical and other non-medical functions such as check in patients, input patient information, handle billing matters, etc. . . . . A portable computer-readable media publisher 111 can also optionally be included on the clerical side 112 for publishing portable computer-readable media to be given to patients leaving the healthcare provider's office. The clinical side 114 can include a medical modality such as the MRI modality 101, a computer terminal 108 that can be utilized by physicians, Reconcilers and Importers, for example, to access Medical Information stored in the PACS server 106 or the memory device 18 in the course of treating a patient, the PACS server 106 itself, and a film printer 110 for printing medical images, for example. The functions performed on the clinical side 114 are primarily performed in the course of providing the actual medical treatment to the patient. As shown, the PACS network 104 also includes a network switch which can be any conventional switch, router or other network hub, and other networking hardware and software to facilitate network communications.

Although the medical modality is shown as an MRI modality 101 in FIG. 3B, it can be any medical modality such as an x-ray machine, MRI scanner, CT scanner, ultrasound, electrocardiograph, PET scanner, or any other suitable medical modality, or any combination thereof. However, for the sake of brevity the examples discussed below describe the modality/modalities as being an MRI modality 101. According to alternate embodiments, there could be a plurality of modalities 101 operatively connected with the PACS network 104 for capturing medical images, medical audio tracks, medical plots, or any combination thereof, to be included in the one or more studies encompassed by the Medical Information. The Medical Information captured by the one or more modalities 101, along with Medical Information imported by the Medical Information importer 10, can be transmitted over the PACS network 104 to be stored in the PACS server 106. According to other embodiments, the Medical Information captured by the MRI or other modality 101 can be transmitted over the PACS network 104 to the Medical Information importer 10. This Medical Information can be locally stored by the Medical Information importer 10 to await reconciliation of at least a portion of the Medical Information with patient information retrieved from a storage location over the communication network before being transmitted to be stored in the PACS server 106 or any other computer-accessible memory operatively connected to the PACS network 104 with the reconciled patient information. For the illustrative examples discussed herein where the Medical Information is to be stored in the PACS server 106, the Medical Information can be stored therein for archival and record-keeping purposes, and in such instances generally can not be altered in the PACS server 106 once stored therein.

Figure 3C:
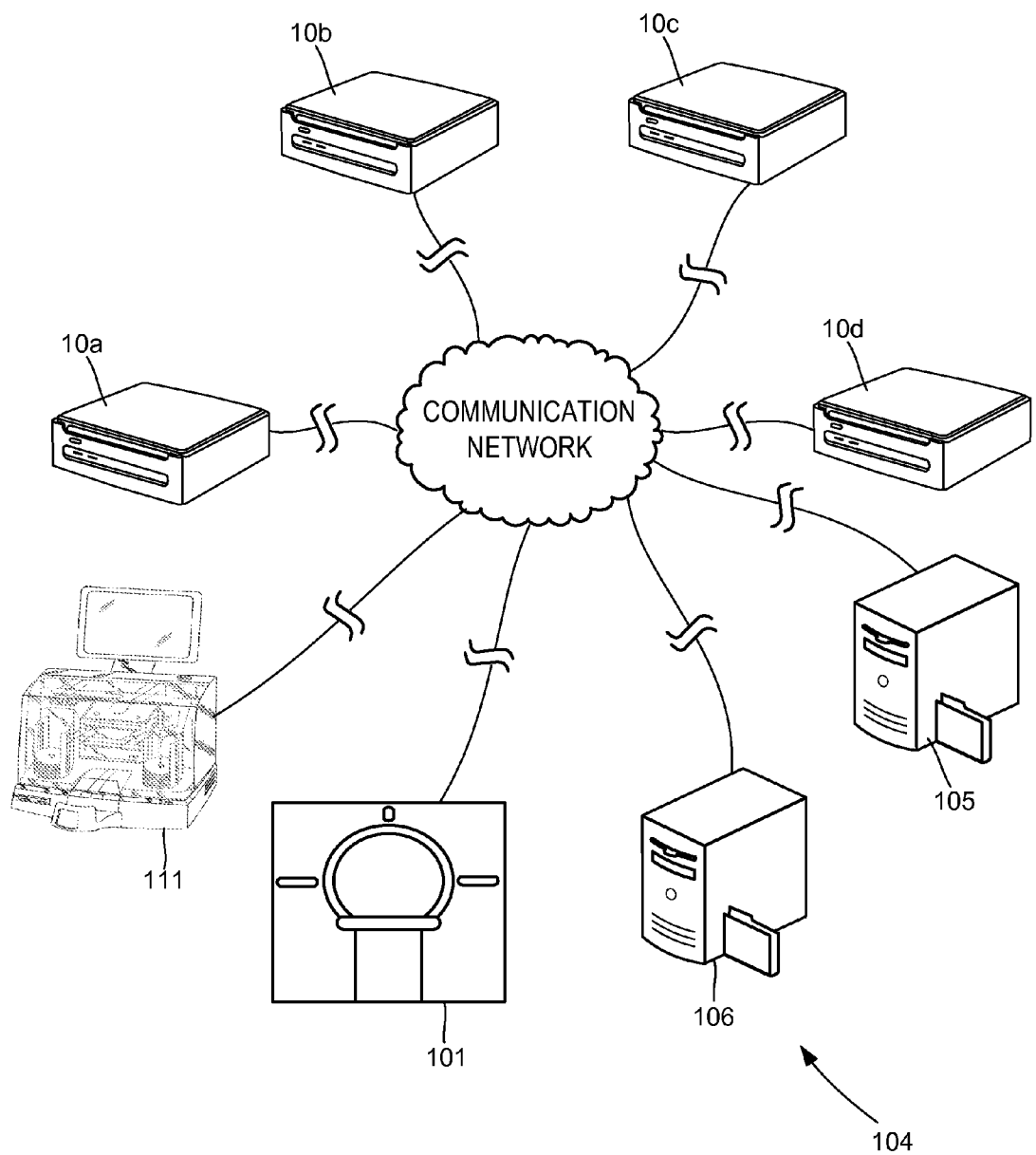
FIG. 3C is an illustrative embodiment of a PACS network comprising a plurality of Medical Information importers, wherein a central Medical Information importer is to receive Medical Information from one or more other Medical Information importers.

Similarly, for the sake of brevity, the examples discussed herein refer to transmitting the Medical Information from the Medical Information importer 10 to be stored in the PACS server 106. However, the Medical Information locally stored by the Medical Information importer 10 can be transmitted over the communication network to stored in any desired destination. For example, the Medical Information can optionally be transmitted to the portable computer-readable media publisher 111 to be stored on a disc 12 or other portable computer-readable medium. According to alternate embodiments, such as the embodiment illustrated in FIG. 3C, the PACS network 104 can include a plurality of Medical Information importers 10a, 10b, 10c, 10d, in addition to at least one of a medical modality 101, PACS server 106, a computer terminal 108, portable computer-readable media publisher 111, and the like. One of the Medical Information importers 10a, 10b, 10c, 10d can be designated as a primary importer 10a to be used to locally store the Medical Information, at least temporarily, as it is being introduced to the PACS network 104 to be subsequently reconciled with existing information and ultimately stored in the PACS server 106 as described below. The other Medical Information importers 10b, 10c, 10d can be distributed to desired locations and networked with the primary importer 10a over the PACS network 104. At least one of the other Medical Information importers 10b, 10c, 10d can optionally be configured to automatically, without operator intervention in response to receiving the Medical Information, transmit the Medical Information over the PACS network 104 to be locally stored, at least temporarily, in the local computer-readable memory (e.g., the memory device 18) provided to the primary importer 10a. The Medical Information can optionally be completely received by the one or more other Medical Information importers 10b, 10c, 10d before the automatic transmission begins, or it can be streamed from the other Medical Information importers 10b, 10c, 10d (i.e., automatic transmission begins before all of the Medical Information is received by the other Medical Information importers 10b, 10c, 10d). From the primary importer 10a, the Medical Information (or at least a portion thereof) can be reconciled with patient information in a database stored on a computer-readable medium operatively connected to the PACS network 104 and ultimately stored in the PACS server 106 as described below.

According to alternate embodiments, the Medical Information importer 10 can optionally be configured to automatically transmit, without operator intervention, the Medical Information over the PACS network 104 to be stored in any remotely-located computer-readable memory. The Medical Information importer 10 can be configured to automatically transmit all received Medical Information over the PACS network 104 upon receipt within the memory device 18 of the Medical Information importer 10. According to other embodiments, the Medical Information importer 10 can be configured to automatically transmit only Medical Information that satisfies a predetermined condition. For example, Medical Information to be delivered to a predetermined person, to a predetermined group of a healthcare provider can be automatically transmitted while Medical Information not satisfying either criterion can be stored, at least temporarily in the memory device 18. Similarly, Medical Information from a predetermined medical modality, and Medical Information associated with a predetermined patient can likewise be automatically transmitted.

A workstation 108, also referred to herein as a computer terminal, which can be a general personal computer, can also be included on the clinical side 114 of the PACS network 104 as shown in FIG. 3B for retrieval and viewing of the Medical Information over the PACS network 104 once the Medical Information has been introduced from the disc 12 by the Medical Information importer 10. Further, as mentioned above, one or more publishing devices such as a film printer 110 and/or a computer-readable media publisher 111, for example, can be included in the PACS network 104 for publishing the Medical Information to be delivered to the patient or other recipient. An example of the computer-readable media publisher 111 is disclosed in the above referenced U.S.

Patent Application Publication No. 2008/0122878 A1 to Keefe et al., the disclosure of which is incorporated in its entirety herein by reference.

The Medical Information importer 10 can be physically located at any desired location with access to the jack 32 (FIG. 2) or other input port to the PACS network 104. In one embodiment, the Medical Information importer 10 can be conveniently located at the receptionist's desk of the medical care provider where patients arrive with their Medical Information on a disc 12. The receptionist or clerical staff can immediately read the Medical Information from the disc 12 and import that Medical Information into the PACS network 104 by simply inserting the disc 12 into the Medical Information importer 10. The auto-run function automatically initiates the importing process without operator intervention once the disc 12 is placed in the Medical Information importer 10.

The illustrative configuration of the PACS network 104 in FIG. 3B can be used to facilitate a split workflow environment. As used herein the phrase "split workflow" refers to dividing the various steps performed herein to import Medical Information from a portable computer-readable medium such as the disc 12 or other source to be stored on a network-accessible computer memory such as that provided to the PACS server 106 among a plurality of different parties. Each of the different parties can optionally be granted different permissions to interact with the Medical Information in a predetermined manner while the Medical Information is locally stored on the Medical Information importer 10, such as that described above for the Reader, Reconciler and Importer. For example, a receptionist logged into the computer terminal 116 may be designated a Reader for purposes of the split workflow, and may be limited to simply reading the medical information from the disc 12 into the internal memory device 18 of the Medical Information importer 10, and optionally viewing the Medical Information. The reader, whose access to the Medical Information can be automatically restricted by the Medical Information importer 10 based on information entered to log into the computer terminal 116, can optionally be restricted from viewing, manipulating, or both viewing and manipulating the medical information so stored. According to alternate embodiments, the reader can optionally be granted permission to supplement the medical information stored in the memory device 18 by inputting patient information such as the patient's name, residential address, or other such non-medical, clerical information via the computer terminal 116. Other examples of patient information can include the patient's sex, date of birth, and patient ID number.

The reception computer terminal 116 and the Medical Information importer 10 can be physically located in the reception area where patients entering the medical facility first arrive to be greeted by the receptionist for administrative purposes. This portion of the PACS network 104 is included on the clerical side 112 of the PACS network 104. At the clerical side 112 the reader can obtain the disc 12 from the patient and insert it into the Medical Information importer 10. An auto-run feature of the Medical Information importer 10 automatically reads the medical information from the disc 12 without further intervention from the reader in stores the medical information in the non-volatile memory device 18.

Individuals such as the so-called Reconcilers and Importers who are logged into the PACS network 104 are granted greater permissions based on their log in information to further interact with the Medical Information stored on the memory device 18 of the Medical Information importer 10 than the reader. The Reconcilers and Importers typically use computer terminals, optionally different terminals allowing them to be logged in at the same time, such as workstation 108 included on the clinical side 114 of the PACS network 104. For example, the Reconciler is granted permission to view the Medical Information stored on the memory device 18 of the Medical Information importer 10 and edit the Medical Information stored in the memory device 18 before the Medical Information is transmitted over the PACS network 104 to be stored in the PACS server 106 or other storage destination. Before being saved to the PACS server 106, at least a portion of the Medical Information can be reconciled with any information for that patient within the PACS server 106, the MWL server, the Radiology Information System ("RIS") server, a Health Information System ("HIS") server, or other electronic database storing patient information that is operatively connected to the PACS network 104 as described in detail below. By reconciling the portion of the Medical Information with the patient's information in the local memory device 18, the Medical Information can be ultimately stored and associated with the patient in a manner consistent with the official patient information maintained by the healthcare provider that permits ready access and retrieval of the Medical Information for that patient in the future. However, the Reconciler is not granted permission to transmit the Medical Information to be stored within the PACS server 106. Once the information has been stored on the PACS server 106 the Medical Information can optionally be designated for deletion on the memory device 18 provided to the Medical Information importer 10, can optionally remain on the memory device 18 until the portion of the memory device 18 occupied by the Medical Information is overwritten, or a combination thereof.

Importers, on the other hand, are granted unlimited permission to access, manipulate and otherwise interact with the Medical Information locally stored by the Medical Information importer 10 in the memory device 18 to be stored on the PACS server 106 or other storage destination. The medical information can be accessed, manipulated, edited, deleted, and otherwise interacted with by the Importer without restriction. The Importer is typically a physician who is treating the patient that is associated with the Medical Information to be stored on the PACS server 106.

As described above, the status of Reader, Reconciler and Importer, each separate individuals, are not necessarily defined by the physical location of those individuals within the PACS network 104. Instead, their respective status defines the extent to which each individual has the ability to interact with the Medical Information and their responsibilities in transferring the Medical Information from the disc 12 to the PACS server 106 or other storage destination. Further, the status of each individual can be automatically established when they log into the PACS network 104 via their respective username and password combinations, for example. In this manner, the receptionist can tend to clerical duties while the Medical Information importer 10 copies the Medical Information from the disc 12 into the memory device 18. Once stored in the memory device 18, the Medical Information becomes available so reconciliation with patient information in a database accessible via the network can be performed by the reconciler, who is logged into the viewing station 108 or other network-connected computer terminal, while the receptionist tends to clerical duties. A different computer terminal can optionally be used by each party having a different role such that the parties involved can simultaneously import and store Medical Information for a plurality of different patients at any given time. The splitting of the tasks to be performed to read and reconcile the Medical Information by separate individuals makes for efficient use of time and system resources while maintaining the confidentiality of the Medical Information. The split workflow system also makes the Medical Information available to the Importer when needed in a timely fashion.

Figure 4:
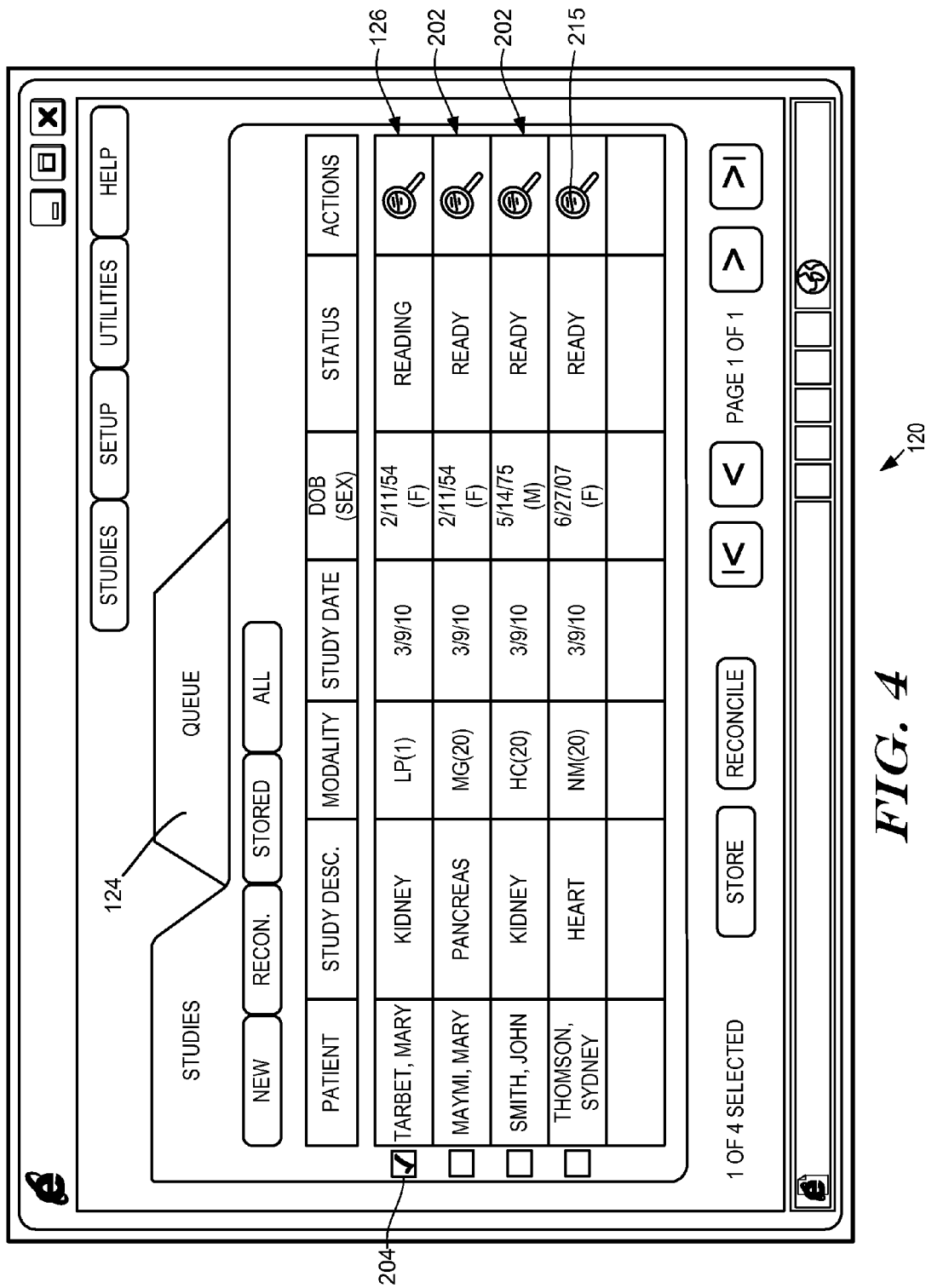
FIG. 4 is an illustrative embodiment of a user interface that allows manipulation of Medical Information displayed in a web browser application that is operational on a workstation operatively connected to a communication network.
Figure 5:
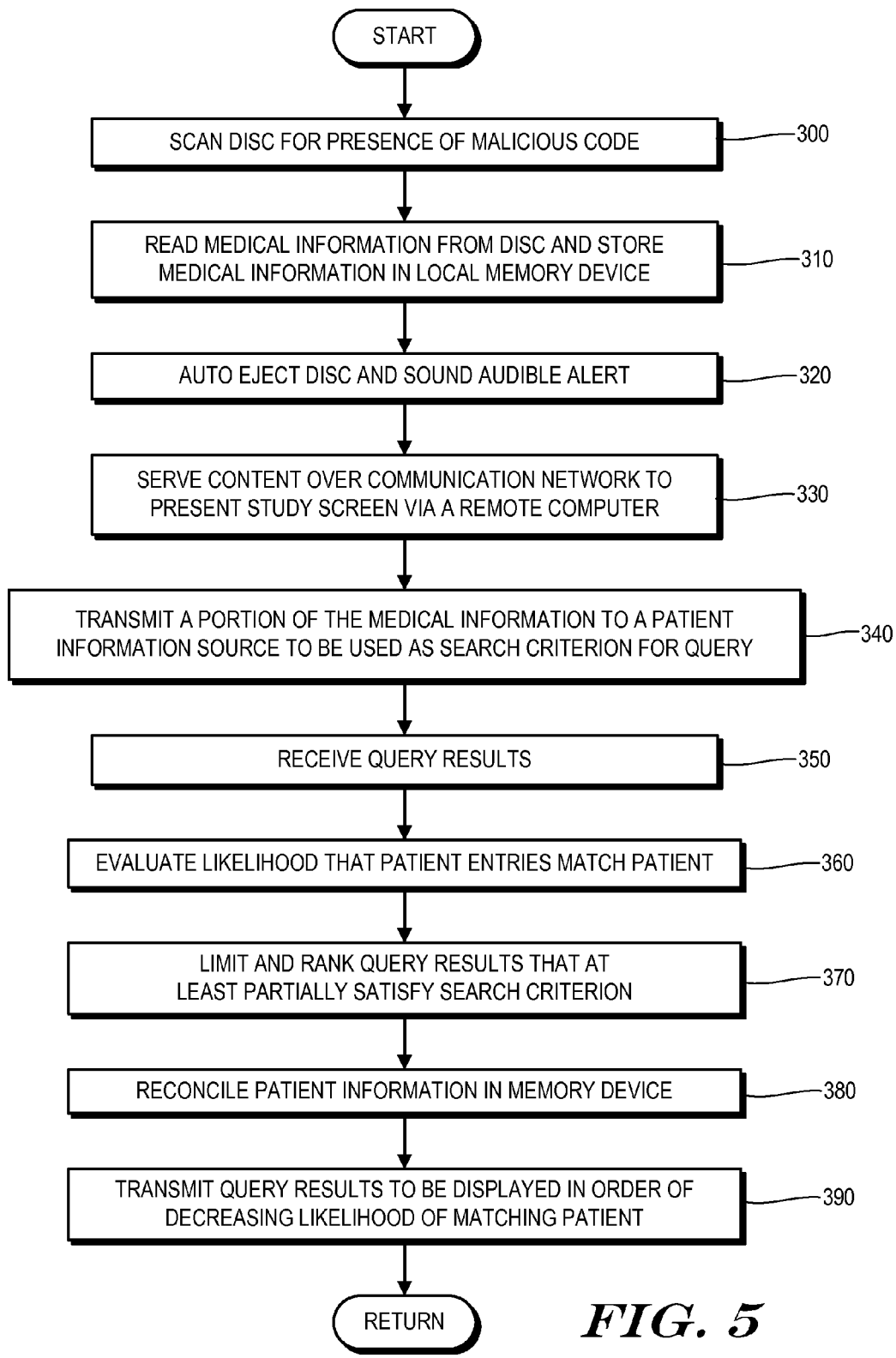
FIG. 5 is a flow diagram graphically depicting an illustrative embodiment of a method of importing medical information from a portable computer-readable medium into a medical network to be stored on a network-connected computer readable medium.
Figure 6:
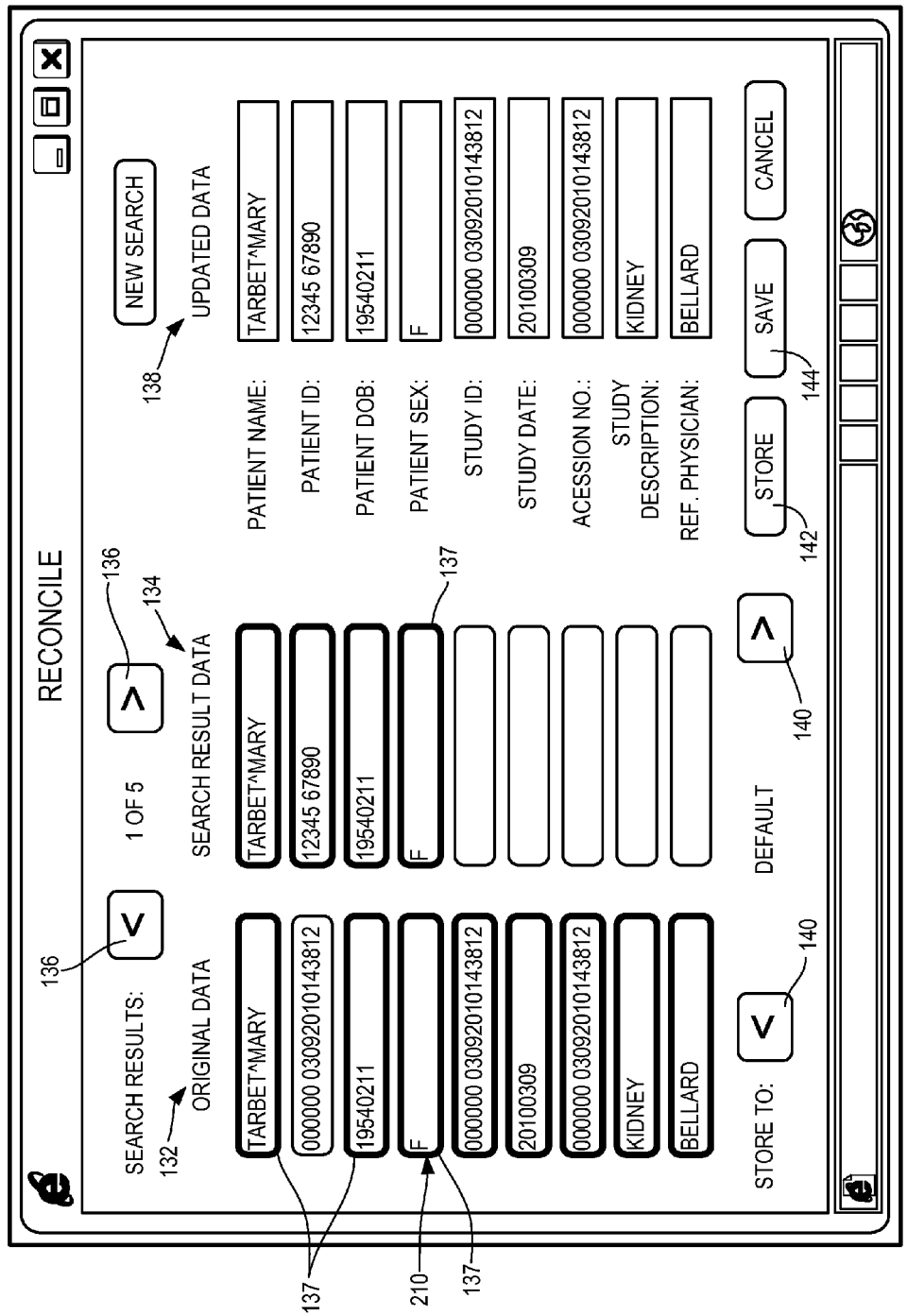
FIG. 6 is an illustrative embodiment of a Reconcile Screen displayed in a web browser application on a display device of a workstation operatively connected to a communication network.

Operation of the Medical Information importer 10 to perform an embodiment of a method of importing Medical Information can be understood with reference to FIGS. 4-6. The illustrative embodiment described with reference to those figures involves introduction of the Medical Information to the Medical Information importer 10 via an optical disc 12. The Medical Information is locally stored by the Medical Information importer 10 on the memory device 18 to ultimately be stored in the PACS server 106. Further, the portion of the Medical Information that can be used to identify the patient is described as being reconciled with patient information retrieved via a query of the RIS server 105, which as shown in FIG. 3B, is separate from the PACS server 106. However, the ultimate storage destination of the Medical Information can be any computer-accessible memory operatively connected to the Medical Information importer 10 via a communication network, and the memory device 18 for locally storing the Medical Information is not necessarily an internal drive of the Medical Information importer 10. Similarly, any portion of the Medical Information can be reconciled with any information that can be obtained via a query of a database operatively connected to the communication network without departing from the scope of the present invention. Likewise, the database queried for information to be reconciled with a portion of the Medical Information can optionally be stored on the same server, such as the PACS server 106 for example, on which the Medical Information is to ultimately be stored according to the method described herein.

In response to the reader inserting the disc 12 into the Medical Information importer 10, the Medical Information importer 10 can initiate the virus scan at step 300 in FIG. 5. Upon a determination that a virus or other malicious code is not present, the Medical Information is automatically extracted from the disc 12 via the autorun feature and stored in the memory device 18 at step 310, from where it can be subsequently associated with the patient who is the subject of the Medical Information and stored in the PACS server 106. Once reading is complete the disc 12 can optionally be automatically ejected, without operator intervention, from the Medical Information importer 10, and audible tones can optionally be broadcast through the speaker 34 to indicate a status of the Medical Information importer 10 at step 320. For example, different audible tones that are universally recognizable and not specific to a particular language for their understanding can optionally be used to indicate the different statuses of the Medical Information importer 10. For instance, a pleasant sounding tone can be used to indicate that reading of the Medical Information has completed and the Medical Information importer 10 is ready to receive additional Medical Information. An abrupt tone can be sounded to indicate the existence of an unexpected or undesirable condition or error such as: corruption of the Medical Information that the Medical Information importer 10 is attempting to receive, that a portable computer-readable medium introduced to the Medical Information importer 10 is not readable or improperly formatted, the absence of Medical Information from a portable computer-readable medium introduced to the Medical Information importer 10, the presence of information other than Medical Information on a portable computer-readable medium introduced to the Medical Information importer 10, detection of a virus or other malicious code on a portable computer-readable medium introduced to the Medical Information importer 10, and the like. According to alternate embodiments, a voice can speak status indicators instead of or in addition to the tones, and the language spoken can optionally be selectable. The memory device 18 acts as a buffer between the disc 12 and the PACS server 106, storing the Medical Information until the Reconciler can reconcile the Medical Information in the memory device 18 with patient information retrieved from the RIS server 105 and the Importer can store the Medical Information in the PACS server 106.

At step 330, the Medical Information importer 10 serves content over the PACS network 104 to be used by the workstation 108 to generate a graphical user interface Study Screen 120 shown in FIG. 4. The Study Screen 120 shown in FIG. 4 can automatically be presented to the reconciler on the workstation 108 of the PACS network 104 in response to storage of the Medical Information in the memory device 18, or can be manually opened by the Reconciler via the workstation 108. Medical Information read from the disc 12 and saved on the memory device 18 of the Medical Information importer 10 is grouped into "jobs" 202, each job 202 forming a row in the Study Screen 120, that can optionally be stored and/or reconciled. According to alternate embodiments, Medical Information can be imported from the disc 12 by inserting the disc 12 into an optical drive provided to the workstation 108 operatively connected to the PACS network 104. This Medical information can be transmitted through the network switch and over the PACS network 104 to the Medical Information importer 10 to be formed into a job 202 to be imported into the PACS network 104 and subsequently stored in the PACS server 106 and/or reconciled with patient information. But regardless of how the Medical Information is imported, each job 202 can represent a collection of Medical Information imported from a different disc 12, said collections being referred to herein as studies. Any networked device with a web browser, such as the workstation 108, that is remotely connected to the Medical Information importer 10 over the PACS network 104 can be used to access the imported Medical Information. Thus, direct access to the Medical Information importer 10 is not necessary, enabling the workflow to be split.

According to an embodiment of the invention, the Medical Information importer 10 includes computer-executable logic in the memory device 18 that can automatically translate text or symbols included in Medical Information from a first language to a second language that is different than the first language. When attempting to reconcile the Medical Information being imported from the disc 12 with other Medical Information corresponding to the patient, another study, or any other record that already exists in the PACS server 106; or when querying or otherwise searching the RIS server 105 the second language can be automatically or manually selected to be the same as the primary language of patient information already stored in the RIS server 105. For example, the computer-executable logic, when executed by the microprocessor 16, can automatically convert Kanji, Katakana and Hiragana Japanese text and characters to Romaji to maximize the likelihood of finding the entry for the patient stored in Romaji within the RIS server 105.

The study screen 120 of FIG. 4 can display each of the jobs stored in the memory device 18. From the study screen 120, one or more of the following functions can be initiated by a party with the proper permission:

Filter, scroll through, and sort the list of studies;
Check the status of a study;

Initiate a study reconciliation with demographic information from Modality Worklist (MWL) and/or Query/Retrieve (Q/R) servers;

Store a study to a desired destination;

Display detailed information about a study;

Delete a study; and

Preview an image within a study.

Once a job has been processed by a Reconciler or Importer and designated to be stored, reconciled or otherwise transmitted from the Medical Information importer 10, that job is transferred to the "Queue" tab 124 that can be selected from the Study Screen 120 in FIG. 4. These jobs remain visible from the Queue tab 124 until the selected process is carried out, at which time they can be removed from the Queue tab 124. According to alternate embodiments, the resolved jobs displayed under the Queue tab 124 that have been stored in the PACS server 106 or other storage destination can optionally remain there with a status that reflects storage of that Medical Information, reconciliation of the Medical Information, etc. . . . . Such entries can be expunged from the queue as new entries are added once the queue has reached the maximum number of entries or can simply expire after a predetermined period of time has elapsed since the Medical Information has been stored.

Reconciling new Medical Information with existing Medical Information allows a reviewing physician, for example, to monitor a patient's progress during a checkup. For instance, if the patient has an initial examination of a broken bone, the patient will likely be referred to a hospital or other care provider to have an x-ray taken if the doctor lacks an x-ray machine in house. When the patient returns with the disc 12 storing the Medical Information in the form of x-ray images, the disc 12 can be inserted into the Medical Information importer 10 and the Medical Information imported. Once imported, the Medical Information can be selected in the study screen 120, shown as the selected study 126 in FIG. 4 identified by a check mark 204, which can be displayed by the workstation 108 in response to selection of the study 126 using a mouse or other conventional input device in a known manner.

Selecting the "Reconcile" button 128 initiates at step 340 in FIG. 5 a reconcile query by the Medical Information importer 10 aimed at retrieving patient information stored on a remotely-located storage device such as the RIS server 105, the PACS server 106 on which the Medical Information is ultimately to be stored, a MWL server, a HIS server, or other patient information source storing patient information with which the portion of the Medical Information is to be reconciled. The reconcile query includes transmitting Medical Information to the patient information source to be compared against existing information stored therein and used as search criteria for locating an existing entry in the Information Source for the patient associated with the Medical Information related to the selected job 126. The patient information transmitted by the Medical Information importer 10 can include a subset of the Medical Information such as patient name, patient ID number, patient sex, patient date of birth, accession number of the study, or personal information such as the patient's residential address or phone number, or a combination thereof, for example. The patient information transmitted to the patient information source for conducting the query can optionally be variable depending on the Medical Information, and can optionally be selected by the Medical Information importer 10 according to the parameters established in the profiles stored on the Smart Drive 42 operatively connected to the Medical Information importer 10. During the reconcile query the patient information, which can optionally be included as a portion of the Medical Information imported from the disc 12, is transmitted to the RIS server 105 in this example to identify a list of patients within the RIS server 105 that are potentially associated with the Medical Information to be stored in the PACS server 106. The patient information transmitted is compared to the existing information in the RIS server 105, and a list of patients possibly associated with the Medical Information to be stored in the PACS server 106 is returned. In response to the query, the query results are returned to the Medical Information importer 10 at step 350 to be transmitted over the PACS network 104 to the workstation 108 and displayed in the "Reconcile" screen 130 shown in FIG. 6. The patients returned can be ranked in an order of decreasing likelihood of being associated with the Medical Information, and can optionally be limited to a predetermined maximum, such as 10 or fewer candidates for example, that is less than the total number of patients in the database. For alternate embodiments, if the patient name and patient date of birth are transmitted, the likelihood of each query result can be evaluated at step 360, and the query results can be limited and optionally ranked at step 370 to existing entries in the RIS server 105 that match both the patient name and patient date of birth. According to alternate embodiments, if no such entry is found, or if one such entry is found and other entries matching one of the two items of the transmitted patient information are found, then the entry matching both search criteria is returned along with the other entries matching one of the two criteria. However, the entry matching both criteria is determined to be the most likely to match the patient that is the subject of the Medical Information, and this entry is ranked to be displayed as the first query result presented to the Reconciler or Importer. According to alternate embodiments, the query results can be limited to only those patient entries matching all of the plurality of search criteria transmitted to conduct the query.

The Medical Information importer 10 can serve content at step 380 over the PACS network 104 to be used by the workstation 108 to display a Reconcile screen 130 as shown in FIG. 6. The content served by the Medical Information importer 10 can present the patients returned by the query in the order of decreasing likelihood, and optionally adjacent to the patient information included in the Medical Information imported from the disc 12 as shown. The query results can optionally include a plurality of patients whose information is to be displayed by the workstation 108 for comparison with the patient information associated with the Medical Information from the disc 12.

The patient information included in the newly-imported Medical Information can be reviewed in the "Original Data" column 132 and compared to patient information corresponding to patients returned from the RIS server 105 by the query displayed in the "Search Result Data" column 134. During the comparison of the patient information associated with the Medical Information being imported and the patient information corresponding to patients returned from the RIS server 105, the Reconcile screen 130 can include an animated appearance, cycling through each entry returned by the query until a plurality of likely matches are identified. Thus, according to an embodiment, the evaluation and limiting steps at 360 and 370 can optionally be performed by the Medical Information importer 10 as it cycles through the query results returned at step 350. Once the plurality of likely matches has been identified based on the comparison of the patient information associated with the Medical Information from the disc 12 and the patient information returned by the query, the first patient entry returned by the reconcile query can be reviewed in the Search Result Data column 134. The patient information, as it is to be updated in the local memory device 18 by the reconciliation of the patient information from the disc 12 with the patient information returned by the query can be automatically populated in the "Updated Data" column 138. The patient information in the Updated Data column 138 will be associated with the rest of the Medical Information and stored with that Medical Information in the PACS server 106. Thus, by reconciling at least a portion of the Medical Information stored locally in the memory device 18 with the information retrieved from the RIS server 105 by the query, the Medical Information, when ultimately transmitted to be stored in the PACS server 106, is stored in a consistent manner, associated with proper patient information for later retrieval from the PACS server 106. The patient information selected from the Original Data and Search Result Data columns 132, 134 for inclusion in the Updated Data column 138 can also be identified with a highlight 137 as shown in FIG. 6. For entries where the information in each of the columns 132, 134 match, such as the patient sex field 210 that shows a value of "F" in each column, both entries can be identified by highlight 137, and "F" is automatically populated in the Updated Data column 138. If the existing patient whose patient information appears in the Search Result Data column 134 does not correspond to the patient associated with the Medical Information from the disc 12 another record returned by the query can be selected using the "Search Results" arrow buttons 136.

The information populating the fields in the "Updated Data" column 138 can be updated by clicking the corresponding field desired in the Original Data column 132 or the Search Result Data column 134 to copy the Medical Information therein to the corresponding field in the Updated Data column 138. For example, if the Reconciler wishes to associate the patient ID "000000 03092010143812" with the Medical Information in the memory device 18 before the Medical Information is transmitted to be stored in the PACS server 106 instead of the patient ID "12345 67890" currently populating the patient ID field in the Updated Data column 138, the Reconciler can simply click on the corresponding field in the Original Data column 132 to insert the value "00000047313298743812" into the Updated Data Column 138 for the patient ID. Alternately, the reconciler can manually type the desired change into the field in the Updated Data column 138. The DICOM Store or other suitable destination can also be selected by using the "Store to" arrows 140 to select the desired storage location on the PACS network 104, such as the PACS server 106, the computer-readable media publisher 111, and the like. A "Store" button 142 can be clicked on to cause, at step 390 in FIG. 5, transmission of the Medical Information stored in the memory device 18 over the PACS network 104 to be stored in the destination(s), which for the present example being described is the PACS server 106, associated with the patient information in the Updated Data column 138. Selecting the Store button 142 can also optionally save the updated patient information in the Updated Data column 138 in the memory device 18 at step 380 to record the association between the patient and the Medical Information being stored locally, in addition to be saved in the PACS server 106. But as described above, the step of storing the Medical Information in the PACS server 106 requires the permission granted to the Importer, and thus, the Store button 142 can optionally be made unavailable for selection by parties lacking the required permission. The patient information to be reconciled with the information in the RIS server 105 can also be saved, as updated, in the local memory device 18 provided to the Medical Information importer 10 at step 380 without transmitting the Medical Information to be stored in the PACS server 106 by simply clicking a "Save" button 144. The Save button 144 allows the reconciled patient information, as it is to be associated with the Medical Information in the PACS server 106, to be saved on the memory device 18 at step 380 without initiating the transmission and storage step of 390. Thus, the Reconciler can update the patient information to include the information that is to be subsequently transmitted to, and stored in the PACS server 106 with the rest of the Medical Information, but can not initiate the transmission and storage of the Medical Information associated with the updated patient information in the PACS server 106.

The Medical Information importer 10 can optionally include a component for serving content over the communication network, said content including a portion of the Medical Information, to provide a party with the appropriate permission to view the Medical Information with a preview of the transmitted portion of Medical Information transmitted. The content served over the communication network can optionally include a medical viewer for presenting the transmitted portion of the Medical Information to the requesting party. For example, an Importer presented with the user interface shown in FIG. 4 can select a preview icon 215. In response to selection of the preview icon, the Importer can be presented with a user interface allowing the Importer to select a portion, optionally less than all, of the Medical Information to be previewed. If the Medical Information is password protected or otherwise secured, the Importer must first enter the password or other key to gain access to the secured portion of the Medical Information the Importer wishes to preview. Upon gaining access to the Medical Information, or if the Medical Information is not secured, the Medical Information importer 10 can serve content over the PACS network 104 that can be used by the workstation 108 or other remotely-located computer to generate the preview to be presented to the Importer.

The portion of the Medical Information previewed can optionally include an entire study, a series of images within the study, or a single image instance within a series including a plurality of images. Further, the preview can be generated before the Medical Information is transmitted over the PACS network 104 to be stored in the PACS server 106. Other embodiments can include transmitting the portion of the Medical Information to be previewed by the Importer over the PACS network 104 from the disc 12 before the Medical Information is completely stored on the memory device 18.

Alternate embodiments also include decrypting or otherwise unsecuring Medical Information stored on the disc 12 in an encrypted or secured format. For example, when a disc 12 storing encrypted Medical Information is introduced to the Medical Information importer 10, the user interface shown in FIG. 4 can present the Reader, Reconciler and/or Importer with a window including a field in which a key code, password or other security deactivation feature can be entered. Reading the secured Medical Information from the disc 12 can optionally be prohibited by the Medical Information importer 10 until the security deactivation feature is entered. According to alternate embodiments, the Medical Information importer 10 can optionally read and store the secured Medical Information in the local memory device 18 without first requiring entry of the security deactivation feature. According to such embodiments, however, the security deactivation feature is required to be entered via a remotely located computer terminal such as the workstation 108 for example, before the Medical Information can be reconciled with patient information, transmitted over the PACS network 104, stored in the PACS server 106, or any combination thereof.

The Medical Information discussed herein can optionally be compliant with a DICOM standard, the IHE Portable Data for Imaging (PDI) and Import Reconciliation Workflow (IRWF) integration profiles, or any other suitable medical standard and/or profile, or any combination thereof.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description, such term is intended to be inclusive in a manner similar to the term "comprising" as "comprising" is interpreted when employed as a transitional word in a claim.

What is claimed is:

1. A medical image importer comprising:
    a housing comprising an external stand-alone form factor for being operatively connected to a communication network via a network interface without a local connection to a computer terminal including a display device;
    an optical drive provided to the housing for reading from an optical computer-readable medium introduced to the optical drive a medical image associated with a patient captured by a medical modality;
    a local, non-volatile computer-readable memory provided to the housing in communication with the optical drive for storing, at least temporarily, the medical image read by the optical drive;
    a controller that is operable to execute computer-executable logic for controlling operation of the medical image importer; and
    an instructional computer-readable memory storing computer-executable instructions to be executed by the controller for performing a method comprising:
        initiating a query of a remotely-located patient information database in communication with the communication network and storing patient information to be associated with the medical image read by the optical drive, said querying comprising transmitting the patient information associated with the medical image over the communication network to identify a patient entry in the patient information database at a time of the query in an attempt to retrieve information specific to the patient;
        serving content, from the medical image importer, over the communication network to be used for generating a display on a remotely-located computer terminal, said display being presentable in an application executed on the remotely-located computer terminal to display at least a portion of the patient information associated with the medical image read by the optical drive and the information specific to the patient associated with the patient entry stored in the patient information database returned in response to said querying;
        updating, in the local computer-readable memory provided to the medical image importer, the patient information read by the optical drive based on the information associated with the patient entry in the patient information database returned in response to said querying, wherein said updating comprises supplementing, changing, or supplementing and changing the patient information read by the optical drive to include at least a portion of the information associated with the patient entry in the patient information database returned in response to said querying, and saving updated information in the local computer-readable memory comprising the patient information as supplemented, changed or supplemented and changed;
        associating the medical image with the patient information updated based on the information associated with the patient entry in the patient information database; and
        transmitting over the communication network the updated information to be stored in a standard-compliant manner in a PACS image database.

2. The medical image importer according to claim 1, wherein the local computer-readable memory and the instructional computer-readable memory comprise different portions of a common memory device provided to the medical image importer.

3. The medical image importer according to claim 1, wherein the instructional computer-readable memory further stores computer-executable instructions that are executable by the controller for transmitting at least a portion of the medical information over the communication network to be received by the computer terminal and displayed in a web-browser application adjacent to a result of said initiating said query for comparison to the result.

4. The medical image importer according to claim 1, wherein the instructional computer-readable memory further stores computer-executable instructions that are executable by the controller for:
    granting a user of the computer terminal permission to view and update the portion of the medical information stored in the local computer-readable memory via the computer terminal; and
    preventing the user of the computer terminal from transmitting the medical information over the communication network to be stored.

5. The medical image importer according to claim 1, wherein the instructional computer-readable memory further stores computer-executable instructions that are executable by the controller for:
    granting a user of another computer terminal permission to view and update the portion of the medical information stored in the local computer-readable memory via the another computer terminal, the another computer terminal being remotely located from the computer terminal and in communication with the medical information importer over the communication network; and
    granting the user of the another computer terminal permission to transmit the medical information over the communication network to be stored in the PACS image database, wherein the user of the another computer terminal is different than the user of the computer terminal.

6. The medical image importer according to claim 5, wherein the instructional computer-readable memory further stores computer-executable instructions that are executable by the controller for:
    granting a third party permission to access the medical information stored in the local computer-readable memory over the communication network and view the medical information; and
    preventing the third party from updating the portion of the medical information and transmitting the medical information over the communication network to be stored in the PACS image database.

7. The medical image importer according to claim 1, wherein the instructional computer-readable memory further stores computer-executable instructions that are executable by the controller for receiving information associated with the patient entry in the PACS image database, wherein granting the user of the computer terminal permission to update the portion of the medical information comprises granting the user of the computer terminal permission to modify the portion of the medical information stored in the local computer-readable memory based on a portion of the information associated with the patient entry in the PACS image database received in response to said initiating said query.

8. The medical image importer according to claim 1, wherein the instructional computer-readable memory further stores computer-executable instructions that are executable by the controller for ranking results returned in response to said initiating the query based on a likelihood that the patient information is to be associated with each of the plurality of entries in the PACS image database, and transmitting content over the communication network for presenting the results returned in predetermined order.

9. The medical image importer according to claim 1, wherein the patient information to be transmitted for said querying is selected according to a configuration parameter of the medical information importer.

10. The medical image importer according to claim 1, wherein the patient information to be transmitted comprises a plurality of criteria comprising at least one of: patient name, patient sex, patient ID number, and patient date of birth.

11. The medical image importer according to claim 1, wherein the patient information to be transmitted comprises alphanumeric characters translated from a first language to a second language.

* * * * *